US007618635B2

(12) United States Patent
Chang et al.

(10) Patent No.: US 7,618,635 B2
(45) Date of Patent: Nov. 17, 2009

(54) SUPER-ANTIGEN FUSION PROTEINS AND THE USE THEREOF

(75) Inventors: Hsiu-Kang Chang, Taipei (TW); Chao-We Liao, Jhunan Township, Miaoli County (TW); Wen-Fang Cheng, Taipei (TW)

(73) Assignee: Healthbanks Biotech Co., Ltd., Taipei (TW)

( * ) Notice: Subject to any disclaimer, the term of this patent is extended or adjusted under 35 U.S.C. 154(b) by 0 days.

(21) Appl. No.: 11/183,796

(22) Filed: Jul. 19, 2005

(65) Prior Publication Data

US 2006/0134753 A1 Jun. 22, 2006

(30) Foreign Application Priority Data

Jul. 21, 2004 (TW) .............................. 93121720 A

(51) Int. Cl.
*A61K 39/00* (2006.01)
*A61K 39/12* (2006.01)
*A61K 39/215* (2006.01)
*A61K 38/00* (2006.01)

(52) U.S. Cl. ............... 424/185.1; 424/186.1; 424/192.1; 424/194.1; 424/221.1; 530/300; 530/323

(58) Field of Classification Search ............... 424/185.1, 424/186.1, 192.1, 221.1; 530/300, 323
See application file for complete search history.

(56) References Cited

U.S. PATENT DOCUMENTS 5,705,163 A * 1/1998 Pastan et al. ............. 424/260.1
6,074,644 A * 6/2000 Pastan et al. ............. 424/178.1

FOREIGN PATENT DOCUMENTS

| CN | 1475571 | | 2/2004 |
|---|---|---|---|
| WO | WO 2004/091524 A | | 10/2004 |
| WO | WO2005/010034 | * | 2/2005 |
| WO | WO 2005/013904 A | | 2/2005 |
| WO | WO 2005/016247 A | | 2/2005 |
| WO | WO 2005/021707 A | | 3/2005 |

OTHER PUBLICATIONS

Che et al., 2003, pp. 637-639; PMID: 12865207, Abstract.*
Olsen et al., Identification of antigenic sites mediating antibody-dependent enhancement of feline infectious peritonitis virus infectivity. J Gen Virol. Apr. 1993;74 ( Pt 4):745-9. .*
He et al., Identification of immunodominant sites on the spike protein of severe acute respiratory syndrome (SARS) coronavirus: implication for developing SARS diagnostics and vaccines J Immunol. Sep. 15, 2005;173(6):4050-7.*
Yang et al., Evasion of antibody neutralization in emerging severe acute respiratory syndrome coronaviruses.Proc Natl Aced Sci U S A. Jan. 18, 2005;102(3):797-801. Epub Jan. 10, 2005.*
Lu et al., Humoral and cellular immune responses induced by SARS or SARS-like coronavirus 3a DNA vaccine in mice.Clin Vaccine Immunol. Nov. 5, 2008. [Epub ahead of print] PMID: 18987164 Abstract.*
Scientific Considerations Related to Developing Follo-On Protein Products. Division of Dockets Management U.S. Food and Drug Administration Nov. 12, 2004, pp. 1-12.*
C.W. Liao et al., "A target-specific chimeric toxin composed of epidermal growth factor and *Pseudomonas* exotoxin A with a deletion in its toxin-binding domain", Appl Microbiol Biotechnol. (1995), 43:498-507.
Jia-Rong Chen et al., "A recombinant chimera composed of repeat region RR1 of *Mycoplasma hyopneumoniae* adhesin with *Pseudomonas* exotoxin: in vivo evaluation of specific IgG response n mice and pigs", Veterinary Microbiology 80 (2001) 347-357.
Jia-Rong Chen et al.,"A recombinant chimera composed of repeat region RR1 of *Mycoplasma hyopenumoniae* adhesin with *Pseudomonas* EXOTOXIN: in vivo evaluatin of specific IgG response in mice and pigs", Veterinary Microbiology (2001), vol. 80, No. 4, pp. 347-357 .
Chien-Fu Hung et al., "Cancer Immunotherapy Using a DNA Vaccine Encoding the Translocation Domain of a Bacterial Toxin Linked to a Tumor Antigen", Cancer Research (2001), vol. 61, No. 9, pp. 3698-3703.
Van Li et al., "Structure-Based Preliminary Analysis of Immunity and Virulence of SARS Coronavirus", Viral Immunology (2004), vol. 17, No. 4, pp. 528-534.

* cited by examiner

*Primary Examiner*—Maria Leavitt
(74) *Attorney, Agent, or Firm*—Hsiu-Ming Saunders; Intellectual Property Connections, Inc.

(57) ABSTRACT

The present invention relates to a super-antigen fusion protein, comprising: a peptide fragment whose sequence corresponds to a partial SARS E2 spike protein; and a translocating peptide fragment for transporting a protein into a cell and translocating the protein in cytosol; wherein, the amino acid sequence of the peptide fragment corresponding to the partial SARS E2 spike protein includes SEQ ID NO. 1, SEQ ID NO. 2, SEQ ID NO. 3 or SEQ ID NO. 4. The present invention further relates to DNA sequences corresponding to the partial SARS E2 spike protein includes SEQ ID NO. 5, SEQ ID NO. 6, SEQ ID NO. 7, or SEQ ID NO. 8; wherein the DNA sequences are able to express specific proteins in an *E. Coli* expression system.

8 Claims, 4 Drawing Sheets

1A

1B

1C

1D

US 7,618,635 B2

SUPER-ANTIGEN FUSION PROTEINS AND THE USE THEREOF

BACKGROUND OF THE INVENTION

1. Field of the Invention

The present invention relates to a super-antigen fusion protein and the use thereof and, more particularly, to a fusion protein which binds to an antigen-presenting cell for inducing antibodies effectively, so as to suppress the virus infection and block the super-antigen response.

2. Description of Related Art

A virus is too small to propagate independently, and has to survive in a host cells by way of parasitism. Hence, viruses are classified in a species between organism and non-organism. Coronavirus is a single-strand RNA virus, and the way it enters cells is by binding to a target cell receptor and forming a cyst, then the virus enters host cells through endocytosis. The viral ribonucleic acid (RNA) reverses to DNA via reverse transcription, and further inserts into chromosomes of the host cell. Therefore, the proteins and genetic materials required for virus growth are produced by the host cell. Under the enzyme catalysis, proteins and genetic materials are assembled and released from the cell, thus the host cell is destroyed.

The virus recognizes the receptors on a cell surface, for example, HIV recognizes CD4 and CCR5 antigens on T lymphocyte surface and then enters the cell. However, coronavirus recognizes aminopeptidase-N on lung or kidney cell surfaces, which is the structure of CD13 receptor, for invasion. Therefore, the main direction in developing biotechnology against viruses is to design a drug to interrupt the interaction between virus and surface antigens, so as to prevent virus invasion. However, besides the structure of the above-mentioned for pathogenesis, some virus has another portion just like a super-antigen to interact with host immune system, which directly binds to a T lymphocyte surface receptor, and then induces interleukin or γ-interferon production heavily from T lymphocyte, resulting in drastically inflammatory response and even triggering the linked T lymphocyte to death (such as programmed cell death apoptosis). Therefore, by elimination of the binding elements of a binding event between super-antigen and cell surface antigen, the viral invasion is suppressed, and the infection symptoms is possibly prevented or alleviated.

T lymphocyte cell membrane exhibits its own T lymphocyte receptor (TCR) in the immune system. There are approximately one million mature T lymphocytes patrolling in the human body. Therefore, TCR is used for monitoring the messages from cells or antigen-presenting cell membranes in the body. An antigen-presenting cell exhibits a Major Histocompatibility Complex (MHC), which is capable of recognizing foreign proteins. MHC and a peptide fragment bind together to form a complex, which is then presented on the surface of cell membrane. Thus, the complex formed by MHC and the peptide will specifically release a message to TCR, which acts as a mediator for self and non-self recognition. However, from the scientific research, it has been found that a certain part of the SARS (severe acute respiratory syndrome) virus envelope spike protein binds to a T lymphocyte receptor after invasion. Moreover, the message of misrecognizing the immune cell results in a release of cytokines immediately without the involvement of MHC molecule through an antigen-presenting cell system. Therefore, T lymphocytes are induced to largely proliferate or produce a vast amount of cytokines, which attack vigorously back to cells and result in inflammatory response. Based on the above study, it is sure that the SARS spike protein exhibits the "super-antigen" property. However, the position of amino acid sequence where the super-antigen fragment is located is still under investigation. Recently, it has been speculated that the super-antigen position is located at the SARS spike protein amino acid sequence 680 to 1050, however, the exactitude needs to be further confirmed.

To prevent the autoimmunological response resulting from SARS virus invasion, a vaccine-like protection system can be utilized. The key point of vaccination is to trigger the originally existing antibody of the infected host with the lymph cell that carries memories of invasion for response. The inventor of the present invention found that the strategy of "induction antibody effectively with a fusion protein" can proceed to a "partial immunization of a super-antigen". The strategy is designed to provide a fusion protein with partial super-antigen of the SARS virus to a healthy human, and a higher titer of antibody is anticipated, wherein the antibody is induced from the immune cells which are capable of recognizing SARS virus super-antigen regions. During infection, the antibody will capture the super-antigen region of SARS virus and this results in alleviating super-antigen induction or inflammatory response without over-stimulating T lymphocyte proliferation. The inventor of the present invention also utilizes the prior investigation of "fusion protein transporting system", to find out the "antibody induction of CD13 cell receptor binding region". Thus, the induced antibody can suppress SARS virus invasion and the SARS infection is prevented.

To begin the experiments for SARS virus investigation, the first concern is to obtain the SARS virus. However, the virus is transmitted by droplet contact, thus the highly infectious virus must be isolated in an appropriately-equipped laboratory. Even though scientists have already sequenced the wild-type SARS virus genome, an ex vivo synthesis of vast amount of viruses is still dependent on a specific host system, which limits the investigation. In the present invention, the inventor translates the amino acid sequence of SARS wild-type virus into specific protein which is published via the Internet. The codons in the amino acid sequence of the SARS virus are modified with translating-effective codons of the ordinary *E. Coli* host system, and the modified sequence is synthesized by sequential PCR. SARS proteins are further expressed effectively by a conventional *E. Coli* host system. The present invention aims to acquire a SARS antigen without adopting a virus gene entity, which is beneficial for SARS virus research.

SUMMARY OF THE INVENTION

The present invention provides a super-antigen fusion protein and the application method thereof, wherein the super-antigen fusion protein comprises a peptide fragment encoding the SARS E2 spike protein, and a translocating peptide. In order to ex vivo obtain the SARS E2 spike protein without infection of the highly infectious virus, the present invention further comprises a nucleic acid sequence encoding super-antigen fusion protein to be expressed as the target protein in the *E. Coli* expression system.

Another object of the present invention is to provide a super-antigen peptide domain which is able to prevent the binding of SARS virus with a T lymphocyte, especially for a peptide domain targeting the E2 spike protein of the SARS virus. Similar to the way of antibody recognition, an E2 spike protein super-antigen peptide domain binds to the position of T lymphocyte where the invasive SARS virus are expected to bind. As a result, immunological responses and allergic reactions are prevented excessive when the invasive SARS virus binds to the T lymphocyte.

Another object of the present invention is to provide a peptide binding domain which prevents the binding of the virus with the T lymphocyte surface receptor CD13, specifically for a peptide targeting the SARS E2 spike protein. Similar to the way of antibody recognition, an E2 spike protein super-antigen peptide domain binds to the position of the T lymphocyte surface receptor CD13 where the invasive SARS virus is expected to bind. The binding mechanism between a virus and the immune T lymphocyte surface receptor CD13 is blocked, which prevents SARS virus invasion through the immune T lymphocyte CD13 binding.

The present invention can be used for detecting SARS virus infection. The induced antibody stimulated by the fusion protein of the present invention prevents the host T lymphocyte from being infected by a virus, and reduces the excessive immunological response and allergic reaction resulting from immune T lymphocyte and SARS virus binding. Therefore, the fusion protein of the present invention is also used for relieving or treating the infection symptoms of the SARS virus.

To achieve the object, the present invention discloses a super-antigen fusion protein, comprising a peptide fragment whose sequence corresponds to at least a partial SARS E2 spike protein. Moreover, a translocating peptide fragment is disclosed for cell binding and translocation, wherein the peptide fragment sequence corresponding to the SARS E2 spike protein includes SEQ ID NO. 1, SEQ ID NO. 2, SEQ ID NO. 3, or SEQ ID NO. 4.

The present invention also comprises a nucleic acid sequence encoding super-antigen fusion protein, the sequence including SEQ ID NO. 5, SEQ ID NO. 6, SEQ ID NO. 7, or SEQ ID NO. 8; wherein, the specific proteins are expressed by the nucleic acid in an *E. Coli* expression system.

The present invention further comprises a peptide for T lymphocyte binding, and the peptide contains at least a partial SARS E2 spike protein, including SEQ ID NO. 1, SEQ ID NO. 2, SEQ ID NO. 3, or SEQ ID NO. 4.

The present invention also comprises a pharmaceutical composition for a peptide binding to a T lymphocyte, comprising a peptide fragment that corresponds to at least a partial SARS E2 spike protein, wherein the peptide fragment corresponding to the SARS E2 spike protein includes SEQ ID NO. 1, SEQ ID NO. 2, SEQ ID NO. 3, or SEQ ID NO. 4.

The peptide sequence of the present invention further comprises a nucleic acid or translocating peptide. The sequence of the translocating peptide is not limited in its category, and mainly has the ability to transport linking peptides into a cell. Preferably, the first and second functional domains of *Pseudomonas* exotoxin A are used for peptide binding and translocating (see U.S. Pat. No. 5,705,163).

The pharmaceutical composition of the present invention also comprises a peptide with amino acids sequence of SEQ ID NO. 1, SEQ ID NO. 2, or the combination thereof, and which is used as a vaccine for stimulating a passive immunological response in a subject. A peptide with amino acids sequence of SEQ ID NO. 3, SEQ ID NO. 4, or the combination thereof is used for producing a vaccine for the SARS virus in a subject.

The super-antigen fusion protein of the present invention comprises four peptide fragments with their amino acid sequences consensus to SARS E2 spike protein sequence (NP_828851) from National Center for Biotechnology Information (NCBI) database. In order to synthesize the SARS E2 spike protein ex vivo, the present invention employs the method disclosed in TW 92126644, to modify the nucleic acid without altering the encoded amino acid for the SARS E2 spike protein partial sequence synthesizing. The modified nucleic acid includes SEQ ID NO. 5, SEQ ID NO. 6, SEQ ID NO. 7, or SEQ ID NO. 8.

Other objects, advantages, and novel features of the invention will become more apparent from the following detailed description when taken in conjunction with the accompanying drawings.

DETAILED DESCRIPTION OF THE PREFERRED EMBODIMENT

Embodiment 1

Figure 1:
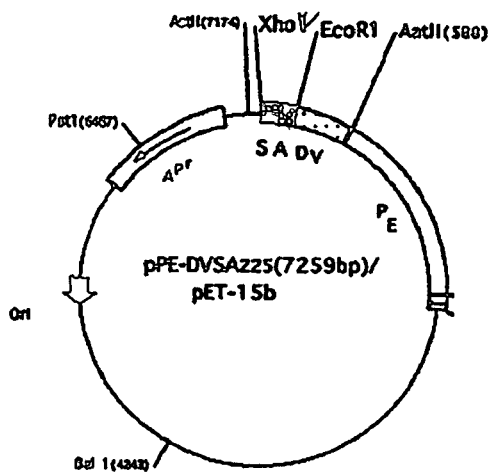
FIG. 1 shows the plasmid map of the embodiment 1 in the present invention. 1A is pET-PE-SA; 1B is pET-PE-SB; 1C is pET-PE-SC; and 1D is pET-PE-SD.
Figure 1:
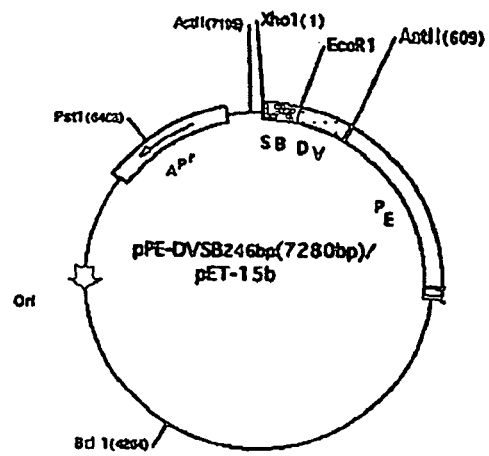
Figure 1:
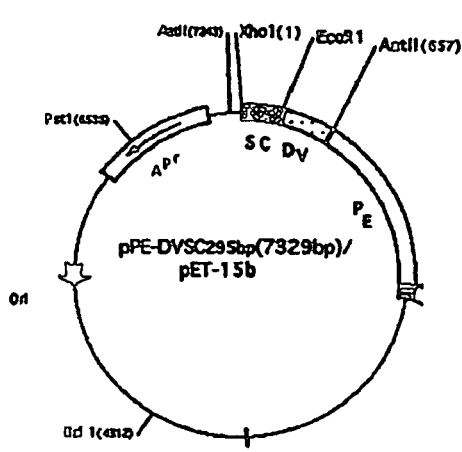
Figure 1:
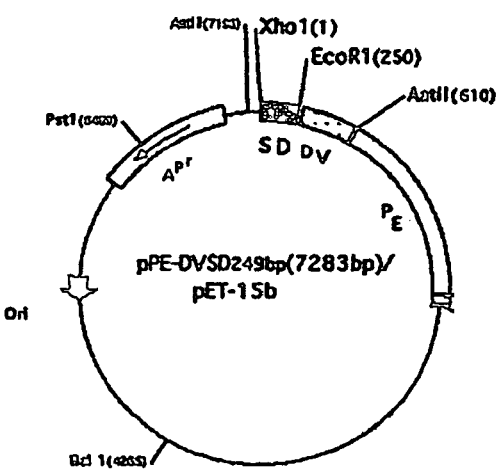

Synthesis of Peptide Encoding a Partial SARS E2 Spike Protein

SARS E2 spike protein sequence (accession number: NP_828851, SEQ ID No. 9) is found in the National Center for Biotechnology Information (NCBI). Position 680 to 1050 of the amino acid sequence (SEQ ID No. 9) is divided into four fragments (SA (SEQ ID NO:1), SB, (SEQ ID NO:2) SC(SEQ ID NO:3), and SD (SEQ ID NO:4)) for nucleic acid modification, and fragment synthesis and amplification, resulting target amino acid sequences ex vivo.

The present invention employs a method disclosed in TW 92126644, and expresses heterogenous virus spike protein in an *E. Coli* expression system. The importance of the modification is to alter a single nucleotide without effecting the original amino acid expression, and further to express specific proteins well in an *E. Coli* host system.

The commercial *E. Coli* plasmid pET230 is used as a template for amplifying nucleic acid fragments with polymerase chain reaction (PCR). In the present embodiment, four synthetic nucleotide fragments are SA (SEQ ID NO:5), SB (SEQ ID NO:6), SC(SEQ ID NO:7) and SD (SEQ ID NO:8). There are 29 pairs of primers used in the fragment amplification, and all the primer sequences are listed in Table 1. The forward primers (F1) are homologous to *E. Coli* plasmid pET230 partial sequence.

TABLE 1

Primer Sequence Design

| Peptide | Sequence | SEQ ID NO | Primer Sequence |
|---|---|---|---|
| SA | SA-F1 | 10 | 5'-CCC TCA GAA TTC GAG AAC ACC ATC GCT ATC CCG A-3' |
|  | SA-R1 | 11 | 5'-GAT GGA GAT GGA GAA GTT GGT CGG GAT AGC GAT GGT GTT CTC GAG TGC TGA GGG-3' |
|  | SA-R2 | 12 | 5'-GGA GGT TTT AGC CAT GGA AAC CGG CAT AAC TTC GGT GGT GAT GGA GAT GGA GAA-3' |
|  | SA-R3 | 13 | 5'-TTC GGT GGA GTC ACC GCA GAT GTA CAT GTT GCA GTC AAC GGA GGT TTT AGC CAT-3' |
|  | SA-R4 | 14 | 5'-GGT GCA GAA GGA ACC GTA CTG CAG CAG CAG GTT AGC GCA TTC GGT GGA GTC ACC-3' |
|  | SA-R5 | 15 | 5'-AGC GAT ACC GGA CAG AGC ACG GTT CAG CTG GGT GCA GAA GGA ACC-3' |
|  | SA-R6 | 16 | 5'-TTT TGA ATT CAC GGG TGT TAC GGT CCT GTT CAG CAG CGA TAC CGG ACA G-3' |
| SB | SB-F1 | 17 | 5'-CCC TCA GAA TTC GAG GTT TTC GCT CAG GTT AAA-3' |
|  | SB-R1 | 18 | 5'-GGT CGG GGT TTT GTA CAT CTG TTT AAC CTG AGC GAA ACC TCG AGT GC TGA GGG-3' |
|  | SB-R2 | 19 | 5'-CAG GAT CTG GGA GAA GTT GAA ACC ACC GAA GTA TTT CAG GGT CGG GGT TTT GTA-3' |
|  | SB-R3 | 20 | 5'-TTC GAT GAA GGA ACG TTT GGT CGG TTT CAG CGG GTC CGG CAG GAT CTG GGA GAA-3' |
|  | SB-R4 | 21 | 5'-ACC AGC GTC AGC CAG GGT AAC TTT GTT GAA CAG CAG GTC TTC GAT GAA GGA ACG-3' |
|  | SB-R5 | 22 | 5'-GTT GAT GTC ACC CAG GCA TTC ACC GTA CTG TTT CAT GAA ACC AGC GTC AGC CAG-3' |
|  | SB-R6 | 23 | 5'-CAG ACC GTT GAA TTT CTG AGC GCA GAT CAG GTC ACG AGC GTT GAT GTC ACC CAG-3' |
|  | SB-R7 | 24 | 5'-CAT GTC GTC GGT CAG CAG CGG CGG CAG AAC GGT CAG ACC GTT GAA TTT-3' |
|  | SB-R8 | 25 | 5'-TTT TGA ATT CCA GAG CAG CGG TGT AAG CAG CGA TCA TGT CGT CGG TCAG-3' |
| SC | SC-F1 | 26 | 5'-CCC TCA GAA TTC GAG GTT TCC GGT ACC GCT ACC GCT-3' |

TABLE 1-continued

Primer Sequence Design

| Peptide | Sequence | SEQ ID NO | Primer Sequence |
|---|---|---|---|
|  | SC-R1 | 27 | 5'-AGC ACC GAA GGT CCA ACC AGC GGT AGC GGT ACC GGA AAC CTC GAG TGC TGA GGG-3' |
|  | SC-R2 | 28 | 5'-AGC CAT CTG CAT AGC GAA CGG GAT CTG CAG AGC AGC ACC AGC ACC GAA GGT CCA-3' |
|  | SC-R3 | 29 | 5'-CAG AAC GTT CTG GGT AAC ACC GAT ACC GTT GAA ACG GTA AGC CAT CTG CAT AGC-3' |
|  | SC-R4 | 30 | 5'-TTT GTT GAA CTG GTT AGC GAT CTG TTT CTG GTT TTC GTA CAG AAC GTT CTG GGT-3' |
|  | SC-R5 | 31 | 5'-GGA GGT GGT GGT CAG GGA TTC CTG GAT CTG GGA GAT AGC TTT GTT GAA CTG GTT-3' |
|  | SC-R6 | 32 | 5'-AGC GTT CTG GTT AAC AAC GTC CTG CAG TTT ACC AGC GGA GGT GGT GGT CAG-3' |
|  | SC-R7 | 33 | 5'-TTT TGA ATT CGG ACA GCT GTT AAC CCA GGG TGT TCA GAG CCT GAG CGT TCT GGT TAAC-3' |
| SD | SD-F1 | 34 | 5'-CCC TCA GAA TTC GAG TCC AAC TTC GGT GCT ATC TCC T-3' |
|  | SD-R1 | 35 | 5'-GAT GTC GTT CAG AAC GGA GGA GAT AGC ACC GAA GTT GGA CTC GAG TGC TGA GGG-3' |
|  | SD-R2 | 36 | 5'-GAT CTG AAC TTC AGC TTC AAC TTT GTC CAG ACG GGA CAG GAT GTC GTT CAG AAC-3' |
|  | SD-R3 | 37 | 5'-GGT CTG CAG GGA CTG CAG ACG ACC GGT GAT CAG ACG GTC GAT CTG AAC TTC AGC-3' |
|  | SD-R4 | 38 | 5'-ACG GAT TTC AGC AGC ACG GAT CAG CTG CTG GGT AAC GTA GGT CTG CAG GGA CTG-3' |
|  | SD-R5 | 39 | 5'-GCA TTC GGA CAT TTT GGT AGC AGC CAG GTT AGC GGA AGC ACG GAT TTC AGC AGC-3' |
|  | SD-R6 | 40 | 5'-TTT ACC GCA GAA GTC AAC ACG TTT GGA CTG ACC CAG AAC GCA TTC GGA CAT TTT-3' |
|  | SD-R7 | 41 | 5'-GTG CGG AGC AGC CTG CGG GAA GGA CAT CAG GTG GTA ACC TTT ACC GCA GAA GTC-3' |
|  | SD-R8 | 42 | 5'-TTT TGA ATT CAA CGT AGG TAA CGT GCA GGA AAA CAA CAC CGT GCG GAG CAG CCT G-3' |

These four peptides are amplified for several times (SA for 6 times, SB for 8 times, SC for 7 times, and SD for 8 times) from PCR by coupling the same forwarded primers (SA-F1 (SEQ ID NO: 10), SB-F1 (SEQ ID NO: 17), SC-F1 (SEQ ID NO: 26), and SD-F1 (SEQ ID NO: 34)) with various reversed primers (SA-R1~R6 (SEQ ID NO: 11-16), SB-R1~R8 (SEQ ID NO: 18-25), SC-R1~R7 (SEQ ID NO: 27-33), and SD-R1~R8 (SEQ ID NO:35-42)). The amplification conditions are: a first cycle for 5 min at 95° C.; a second cycle for 1 min at 94° C., 0.5 min at 55° C., and 1 min at 72° C. of 20 cycles; and a third cycle for 1 min at 72° C.

After amplification, the PCR products are visualized in the agarose gel electrophoresis. The representatives are cut and eluted from gel slices.

Embodiment 2

Plasmid Construction

Four nucleotides SA (SEQ ID NO:5), SB (SEQ ID NO:6), SC(SEQ ID NO:7), and SD (SEQ ID NO:8) from PCR, and plasmid pET-PE which contains binding domain and translocating domain of *Pseudomonas* exotoxin A (see Liao C. W. et al., Applied Microbiol Biotechnol 143:498-507, 1995), are ligated together in the restriction enzyme site respectively. Four constructed fusion plasmids are obtained and named pET-PE-SA, pET-PE-SB, pET-PE-SC, and pET-PE-SD (FIG. 1).

Embodiment 3

Protein Expression and Purification

According to the method from Sambrook (Sambrook et al., J. Neuroimmunol. 1991; 32(1):35-41), the four plasmids, pET-PE-SA, pET-PE-SB, pET-PE-SC, and pET-PE-SD, were expressed to obtain fusion proteins by using IPTG induction method.

The *E. Coli* strain for protein (peptide) expression was BL21 (DE3) pLysS. First, the picked colony was inoculated into 100 ml of LB medium containing 200 μg/ml of ampicillin until $OD_{550}$ reached approximate 0.3. Second, 1 mM IPTG (isopropylthio-β-D-galactoside, Promege, USA) was added into the medium, the incubation was carried on for 90 min, and cells were centrifuged and collected. The membranes of the cells carrying the target protein were loosen by freezing and thawing repeatedly, and then 10 ml lysis buffer (which contains 0.9 mg/ml lysozyme, 1 ml PMSF and 0.064 mg/ml DNaseI) was added for 10 min treatment at room temperature. Then, 1 ml 10% TRITON® X-100 was added for another 10 min treatment at room temperature. The mixture was centrifuged at 12000×g for 10 min to collect the protein. Then, the collected inclusion body was dissolved in 4 ml 8M urea.

Furthermore, the commercial pET His-Taq purification system (Novagen, USA) is performed according to the instructions. The cell inclusion body is dissolved in 4 ml ice cold binding buffer (which contains 5 mM imidazole, 0.5 M NaCl, and 20 mM Tris-HCl, pH7.9) with sonication until the inclusion body disperses. Then, the mixture is centrifuged in 1200×g for 15 min at 4° C., and the supernatant is poured into a column (which is the His-Bind metal chelating resin immobilized with $Ni^{2+}$). Finally, the protein binding to column is eluted and collected with a buffer (which contains 0.5 M imidazole, 0.5 M NaCl, and 20 mM Tris-HCl, pH7.9).

Four fusion proteins, i.e. PE-SA (SEQ ID NO:43), PE-SB (SEQ ID NO:44), PE-SC(SEQ ID NO:45), and PE-SD (SEQ ID NO:46), have been expressed from fusion plasmids in the same process.

Embodiment 4

Cellular Immunity Test

A. Isolation of Peripheral Blood Monocytes

The blood of a healthy adult was obtained and mixed with the Hanks' balanced salt solution (Hanks' balanced salt solution kit, Life Technologies, Rockville, Md.) at a 1:1 ratio.

According to the method from Sacerdote (Sacerdote et al., J. Neuroimmunol 1991; 32(1):35-41), the Ficoll-Paque solution (Amersham Biosciences, Uppsala, Sweden) was used for isolating peripheral blood monocytes. The mixture of blood and Ficoll-Paque solution was centrifuged (600×g, 30 min), and then the solution with monocytes was removed to another centrifuge tube. The mixture was washed twice with Hanks' balanced salt solution and centrifuged at 1200×g for 10 min to obtain the isolated peripheral blood monocytes.

According to the method from Gong (Gong et al., J. Immunol., 2000; 165(3):1705-11), the immature peripheral blood monocytes have the potential to proliferate into dendritic cells (DCs). Peripheral blood monocytes were dispersed in the cell culture medium to allow cells to attach to the culture dish, thereafter the cells were incubated for 2 hr at 37° C. Then, the unattached cells were removed. The cells were incubated with 1% human serum RPMI 1640 (Mediatech, Herndon, Va.) medium and GM-CSF (800 IU/ml) and IL-4 (500 U/ml) for 6 days. The cytokines were added on Day 0, Day 2, or Day 4. On Day 6, the unattached cells were collected to analyze the molecular marker of the dendritic cells.

The collected dendritic cells are washed with a FACScan buffer consisting of PBS, 0.2% FBS, and 0.5% sodium azide. Further, the FITC- or PE-conjugated anti-human antibodies (CD1a, CD3, CD56, CD80, HLA-A, B, C, and HLA-DR; PharMingen, San Diego, Calif.) are added to the cells for 30 min on ice. Again, the cells are washed with the FACScan buffer. The data is analyzed with FACScalibur flow cytometer (Becton Dickinson, Mountain View, Calif.) and "CellQuest" software.

B. IFN-γ Enzyme-Linked Immunospot Assay (Elispot Assay)

According to the articles from Miyahira et al. (Miyahira et al., J Immunol Methods, 1995; 181(1):45-54) and Murali-Krishna et al. (Murali-Krishna et al., Immunity, 1998; 8(2): 177-87), enzyme-linked immunospot assay was modified to estimate the specificity for SA, SB, SC, and SD antigens with CD8+ T lymphocytes.

A layer of anti-human INF-7 antibody (10 μg/ml; PharMingen) in PBS (50 μl) was covered on a 96-well dish (Millipore, Bedford, Mass.) and cultured at 4° C. for overnight. Then, the cultured wells were washed and coated with 10% fetal bovine serum (FBS) medium. Moreover, different amounts of fresh or cultured peripheral blood monocytes were prepared, and further mixed with proliferated dendritic cells at a 10:1 ratio (as described in the Embodiment 3). An amount of $1 \times 10^6$ of dendritic cells were added into each cultured well coated with FBS, wherein the cells were untreated or treated with four fusion proteins PE-SA (SEQ ID NO:43), PE-SB (SEQ ID NO:44), PE-SC (SEQ ID NO:45), and PE-SD (SEQ ID NO:46), for 2 hr, respectively.

After incubation, the cultured wells were washed again. A biotin-conjugated rat anti-human INF-γ antibody (5 μg/ml; PharMingen) in PBS (50 μl) was added and incubated overnight at 4° C. Then, the dish was washed for six times. 1.2 μg/ml of avidin-alkaline phosphatase (Sigma, St. Louis, Mo.) in 50 μl PBS was added and incubated for 2 hr at room temperature. Further, 50 μl of 5-bromo-4-chloro-3-indolyl phosphate/nitroblue tetrazolium solution (Boehringer Mannheim, Indianapolis, Ind., USA) was added for 20 min at room temperature, and the spots were observed. The substrate solution was removed, and the cultured wells were washed with water to stop the reaction. Finally, the cultured wells were dried and the spot amount was counted under an anatomic microscopy.

Figure 2:
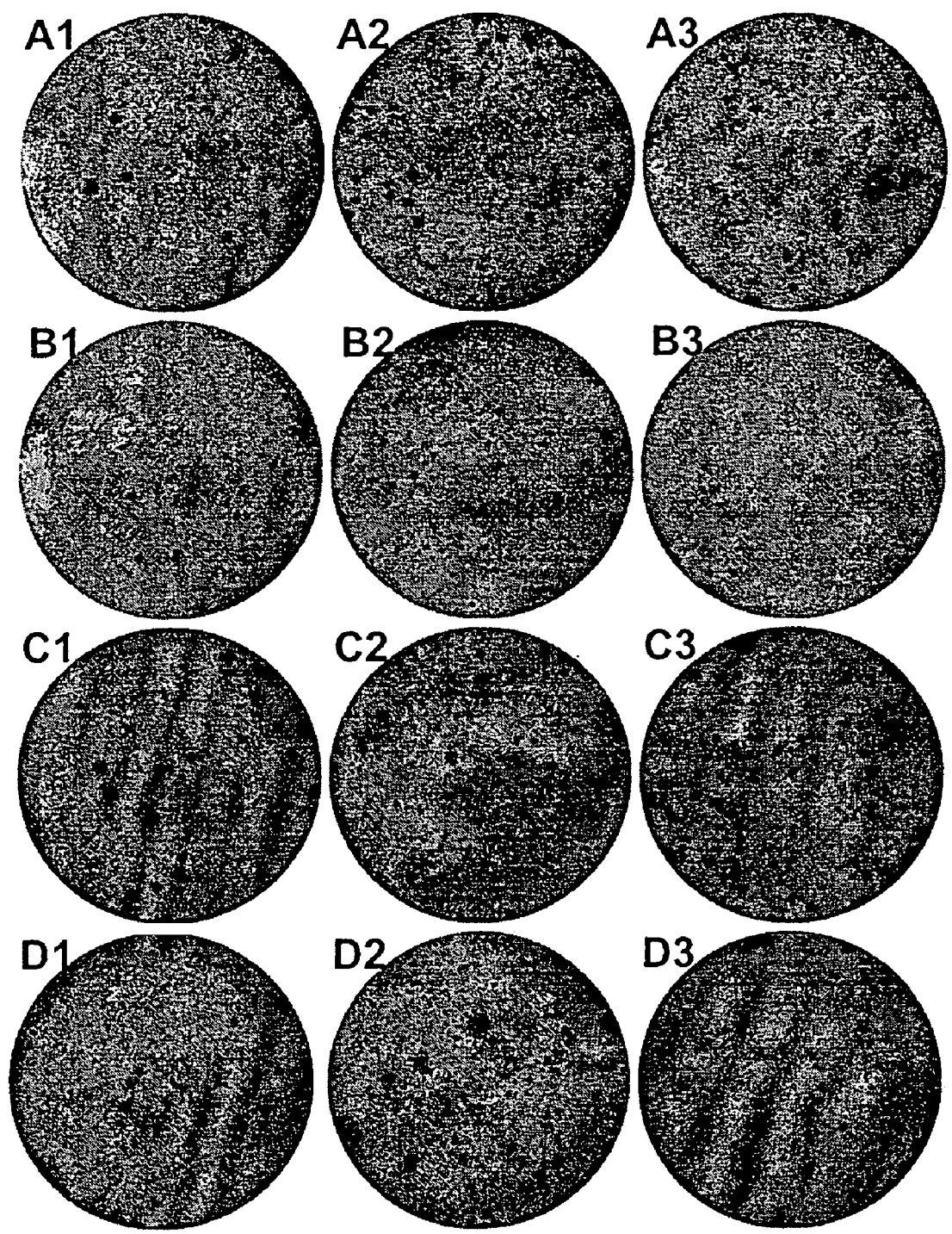
FIG. 2 is the enzyme-linked immunospot assay (ELISPOT assay) of the embodiment 3B in the present invention. The result shows the interactions of the fusion proteins (PE-SA, PE-SB, PE-SC and PE-SD) and the monocytes of human peripheral blood after various incubation periods. A1 is the result with PE-SA fusion protein; A2 is the result with PE-SA fusion protein after 7 days incubation; A3 is the result with PE-SA after 14 days incubation. B1 is the result with PE-SB fusion protein; B2 is the result with PE-SB after 7 days incubation; B3 is the result with PE-SB after 14 days incubation. C1 is the result with PE-SC fusion protein; C2 is the result with PE-SC after 7 days incubation. C3 is the result with PE-SC after 14 days incubation. D1 is the result with PE-SD fusion protein; D2 is the result with PE-SD after 7 days incubation; D3 is the result with PE-SD after 14 days incubation.
Figure 3:
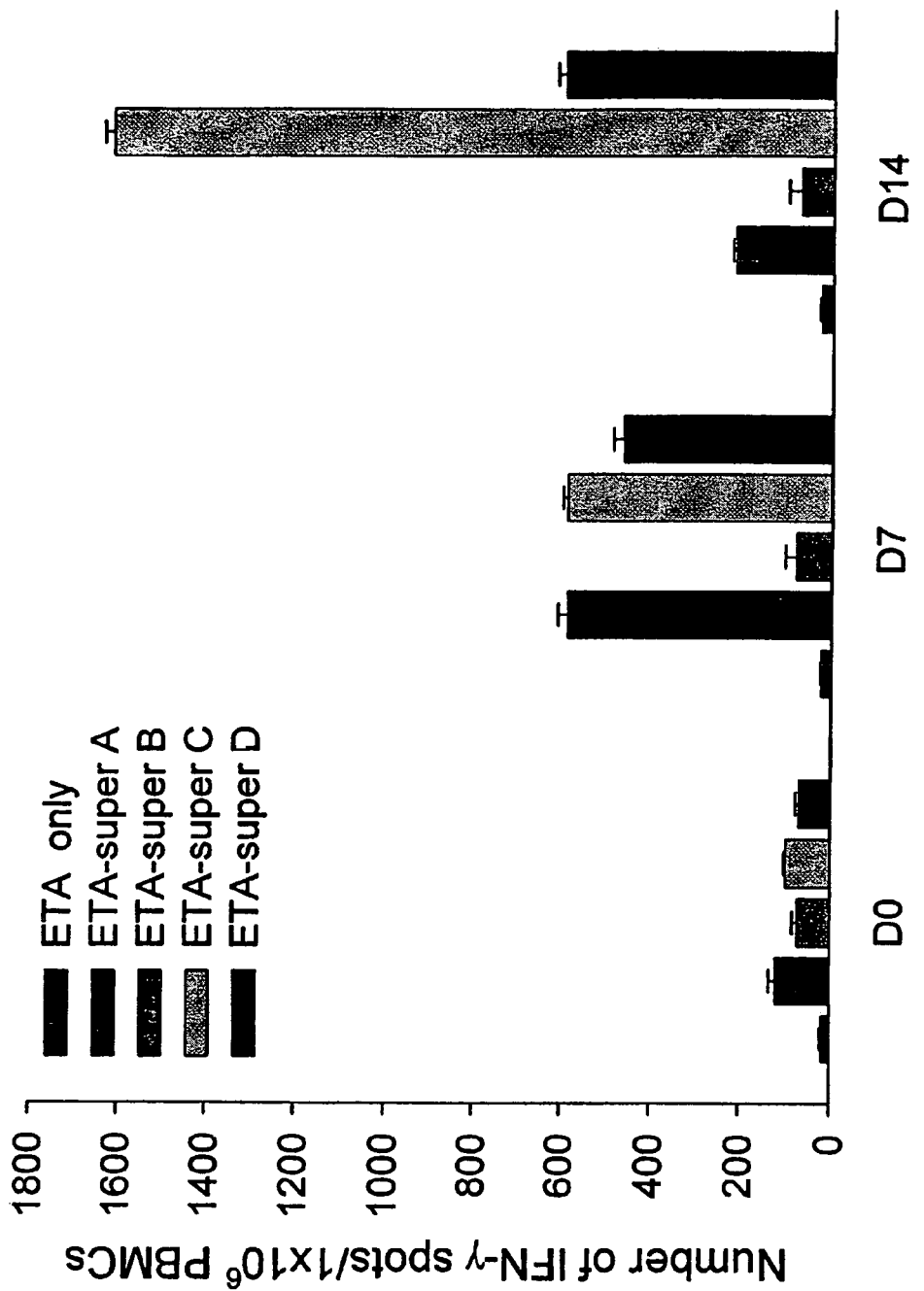
FIG. 3 is the bar chart illustrating the result of the Embodiment 4, where the spots in FIG. 2 are counted and shown in the bar chart.

An enzyme-linked immunospot assay was used for evaluating the amount of CD8+ T lymphocytes reflected from PE-SA (SEQ ID NO:43), PE-SB (SEQ ID NO:44), PE-SC (SEQ ID NO:45), and PE-SD (SEQ ID NO:46) fusion protein treatment. FIG. 2 shows the result of enzyme-linked immunospot assay, which represents the reactions from different incubation times. The spots were counted and shown in a bar chart as in FIG. 3. From the figure, it was observed that on the seventh day after immunizing, serum IFN-γ production is elevated in mice injected with PE-SA (SEQ ID NO:43), PE-SC (SEQ ID NO:45), and PE-SD (SEQ ID NO:46) fusion protein. On the fourteenth day after immunizing, PE-SC (SEQ ID NO:45) fusion protein elicited a severe immunological response and induced a high amount of IFN-γ in mice.

Embodiment 5

Animal Immunity Test

A. Animal Preparation

Six to eight week-old female mice C57BL/6J are purchased from National Taiwan University (Taipei, Taiwan), and are fed in the Animal Center of National Taiwan University Hospital.

B. Animal Immunity

The fusion proteins, i.e. PE-SA (SEQ ID NO:43), PE-SB (SEQ ID NO:44), PE-SC(SEQ ID NO:45), and PE-SD (SEQ ID NO:46), prepared from Embodiment 2 are injected individually into each mice in an amount of 100 μg for immunological response observation. Meanwhile, another group of mice is prepared for injecting with *Pseudomonas* exotoxin A peptide only as the control. The administering schedule is Day 0, Day 14, and Day 28 while initiating the experiment.

C. Antibody Specificity Test

According to the method from Cheng (Cheng et al., J. Clin. Invest., 2001; 108(5):669-78), i.e., enzyme-linked immunoabsorbent assay (ELISA), serum PE-SA (SEQ ID NO:43), PE-SB (SEQ ID NO:44), PE-SC (SEQ ID NO:45), and PE-SD (SEQ ID NO:46) antibody is specificities were evaluated, respectively. A 96-well dish was covered with a layer of PE-SA (SEQ ID NO:43), PE-SB (SEQ ID NO:44), PE-SC (SEQ ID NO:45) (5 μg) fusion proteins, respectively, for overnight culturing at 4° C. Then, 20% fetal bovine serum (FBS) in PBS was coated into culture well. Mice serum was obtained after 14 days of immunization, and serially diluted with PBS and then added into cultured wells for 2 hr at 37° C. Furthermore, cultured wells were washed with 0.05% TWEEN® 20 in PBS, and a 1:2000 peroxidase-conjugated rabbit anti-mouse IgG antibody (Zymed, San Francisco, Calif.) was added for 1 hr at room temperature. After washing, 1-STEP™ Turbo TMB-ELISA (Pierce, Rockford, Ill.) was added to develop the color. Finally, the reaction was stopped by adding 1M $H_2SO_4$. The result was read at the 450 nm absorbance spectra in an ELISA reader.

Figure 4:
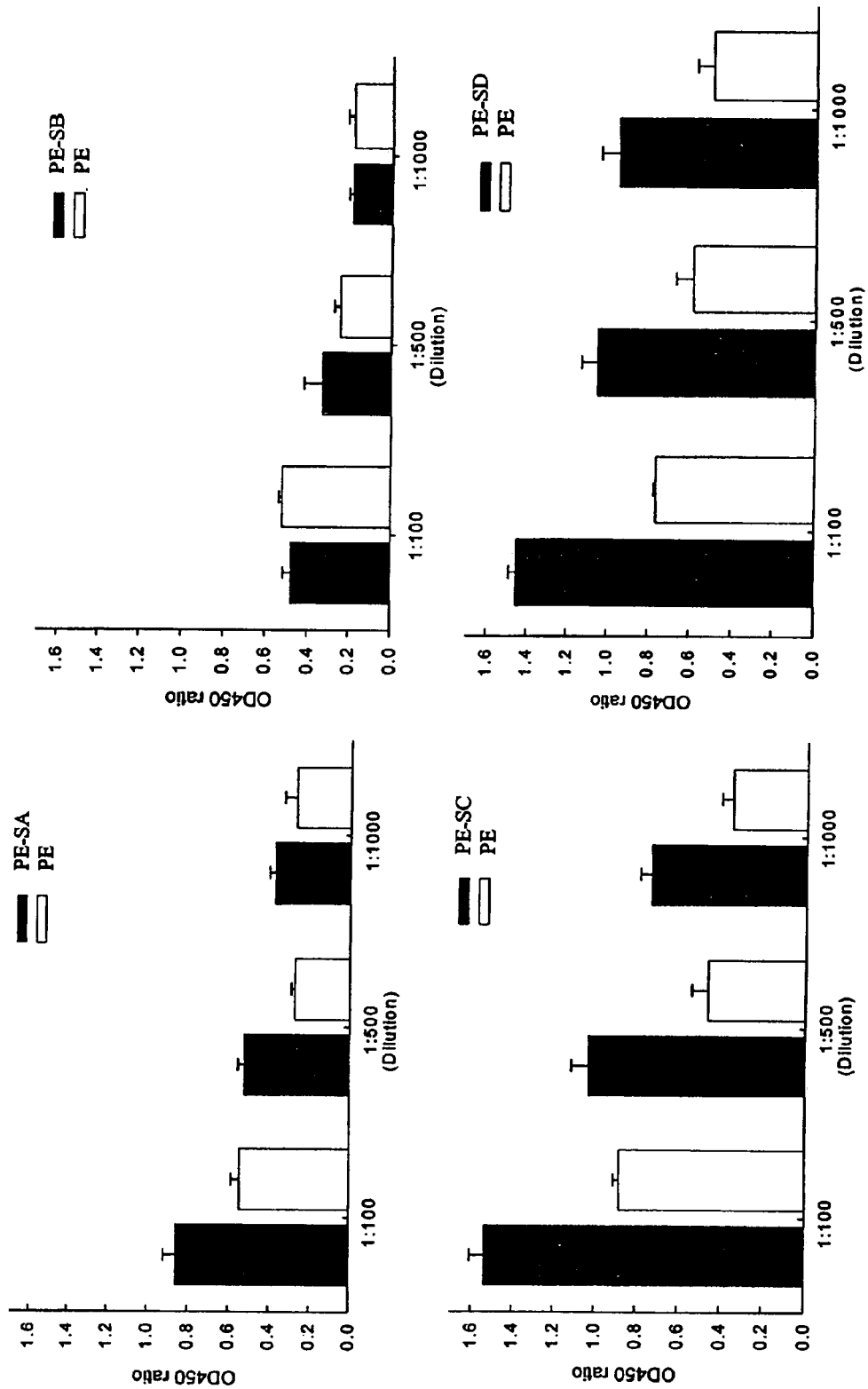
FIG. 4 is the antibody titer determination of the Embodiment 4 in the present invention. A, B, C, and D represents the fusion proteins consisting of the PE translocation peptide and SA, SB, SC, or SD peptide fragments respectively. The solid bar represents the present fusion protein, and the hollow bar represents the peptide simply encoding the PE translocation protein.

FIG. 4 is the titer estimation of specific antibody with the serum diluted serially at the ratio of 1:100, 1:500 and 1:1000. The result shows that the CD8+ cell amount in mice serum injected with PE-SC(SEQ ID NO:45) and PE-SD (SEQ ID NO:46) fusion protein is higher than that of the serum from PE-SA (SEQ ID NO:43) and PE-SB (SEQ ID NO:44) fusion protein injected mice ($P<0.01$, one-way ANOVA). Herein, it is found that PE-SC(SEQ ID NO:45) and PE-SD (SEQ ID NO:46) fusion protein could stimulate higher antibody in animals. Thus, in clinical tests, a subject accepting PE-SC (SEQ ID NO:45) and PE-SD (SEQ ID NO:46) fusion protein will produce an antibody for the SARS virus and protect oneself form infection.

The fusion proteins of the present invention successfully induce antibody production in animals. For large amounts of IFN-γ production induced by PE-SC(SEQ ID NO:45) and PE-SD (SEQ ID NO:46) fusion protein, it is observed that in the present embodiment, the amino sequences of SC and SD peptides are possibly located in the super-antigen positions of SARS virus. Therefore, the excessive immunological response occurs in an antibody-inducting animal injected with PE-SC(SEQ ID NO:45) and PE-SD (SEQ ID NO:46) fusion protein, and the immunological response is not harmful to an animal. For another aspect, the large amount of specific antibodies in animals, induced from PE-SC(SEQ ID NO:45) and PE-SD (SEQ ID NO:46) fusion protein enables the vaccine manufacture in the future and has the potential for SARS therapy.

Furthermore, the present PE-SA (SEQ ID NO:43) and PE-SB (SEQ ID NO:44) fusion protein do not induce excessive immunological response in animals. Thus, it is possible to stimulate passive immunity in an animal tending to be infected with the SARS virus. In animals, the binding mechanism of the SARS spike protein and T lymphocyte surface receptor CD13 can be blocked by simply administering PE-SA (SEQ ID NO:43) and PE-SB (SEQ ID NO:44) fusion proteins, and thus prevent the SARS virus infection.

Although the present invention has been explained in relation to its preferred embodiment, it is to be understood that many other possible modifications and variations can be made without departing from the spirit and scope of the invention as hereinafter claimed.

What is claimed is:

1. A super-antigen fusion protein for inducing antibodies against severe acute respiratory syndrome (SARS) E2 spike protein consisting of:
   (a) a peptide fragment of SARS E2 spike protein consisting of the amino acid sequence of SEQ ID NO: 1;
   (b) a peptide fragment of *Pseudomonas* exotoxin (PE) consisting of a binding domain and a translocation domain; and
   (c) a restriction enzyme site linker connecting said peptide fragment of the SARS E2 spike protein to said peptide fragment of PE.

2. A super-antigen fusion protein for inducing antibodies against SARS E2 spike protein consisting of:
   (a) a peptide fragment of SARS E2 spike protein consisting of the amino acid consisting of the amino acid sequence of SEQ ID NO: 2;
   (b) a peptide fragment of *Pseudomonas* exotoxin (PE) consisting of a binding domain and a translocation domain; and
   (c) a restriction enzyme site linker connecting said peptide fragment of the SARS E2 spike protein to said peptide fragment of PE.

3. A super-antigen fusion protein for inducing antibodies against SARS E2 spike protein consisting of:
   (a) a peptide fragment of SARS E2 spike protein consisting of the amino acid consisting of the amino acid sequence of SEQ ID NO: 3;
   (b) a peptide fragment of *Pseudomonas* exotoxin (PE) consisting of a binding domain and a translocation domain; and
   (c) a restriction enzyme site linker connecting said peptide fragment of the SARS E2 spike protein to said peptide fragment of PE.

4. A super-antigen fusion protein for inducing antibodies against SARS E2 spike protein consisting of:
   (a) a peptide fragment of SARS E2 spike protein consisting of the amino acid consisting of the amino acid sequence of SEQ ID NO: 4;
   (b) a peptide fragment of *Pseudomonas* exotoxin (PE) consisting of a binding domain and a translocation domain; and
   (c) a restriction enzyme site linker connecting said peptide fragment of the SARS E2 spike protein to said peptide fragment of PE.

5. A pharmaceutical composition for inducing antibodies against SARS E2 spike protein comprising the super-antigen fusion protein of claim 1.

6. A pharmaceutical composition for inducing antibodies against SARS E2 spike protein comprising the super-antigen fusion protein of claim 2.

7. A pharmaceutical composition for inducing antibodies against SARS E2 spike protein comprising the super-antigen fusion protein of claim 3.

8. A pharmaceutical composition for inducing antibodies against SARS E2 spike protein comprising the super-antigen fusion protein of claim 4.

* * * * *

SEQUENCE LISTING

```
<160> NUMBER OF SEQ ID NOS: 9

<210> SEQ ID NO 1
<211> LENGTH: 71
<212> TYPE: PRT
<213> ORGANISM: SARS coronavirus

<400> SEQUENCE: 1
```

```
Asn Thr Ile Ala Ile Pro Thr Asn Phe Ser Ile Ser Ile Thr Thr Glu
1               5                   10                  15

Val Met Pro Val Ser Met Ala Lys Thr Ser Val Asp Cys Asn Met Tyr
            20                  25                  30

Ile Cys Gly Asp Ser Thr Glu Cys Ala Asn Leu Leu Leu Gln Tyr Gly
            35                  40                  45

Ser Phe Cys Thr Gln Leu Asn Arg Ala Leu Ser Gly Ile Ala Ala Glu
        50                  55                  60

Gln Asp Arg Asn Thr Arg Glu
65              70
```

<210> SEQ ID NO 2
<211> LENGTH: 97
<212> TYPE: PRT
<213> ORGANISM: SARS coronavirus

<400> SEQUENCE: 2

```
Val Phe Ala Gln Val Lys Gln Met Tyr Lys Thr Pro Thr Leu Lys Tyr
1               5                   10                  15

Phe Gly Gly Phe Asn Phe Ser Gln Ile Leu Pro Asp Pro Leu Lys Pro
            20                  25                  30

Thr Lys Arg Ser Phe Ile Glu Asp Leu Leu Phe Asn Lys Val Thr Leu
            35                  40                  45

Ala Asp Ala Gly Phe Met Lys Gln Tyr Gly Glu Cys Leu Gly Asp Ile
        50                  55                  60

Asn Ala Arg Asp Leu Ile Cys Ala Gln Lys Phe Asn Gly Leu Thr Val
65                  70                  75                  80

Leu Pro Pro Leu Leu Thr Asp Asp Met Ile Ala Ala Tyr Thr Ala Ala
                85                  90                  95

Leu
```

<210> SEQ ID NO 3
<211> LENGTH: 90
<212> TYPE: PRT
<213> ORGANISM: SARS coronavirus

<400> SEQUENCE: 3

```
Val Ser Gly Thr Ala Thr Ala Gly Trp Thr Phe Gly Ala Gly Ala Ala
1               5                   10                  15

Leu Gln Ile Pro Phe Ala Met Gln Met Ala Tyr Arg Phe Asn Gly Ile
            20                  25                  30

Gly Val Thr Gln Asn Val Leu Tyr Glu Asn Gln Lys Gln Ile Ala Asn
            35                  40                  45

Gln Phe Asn Lys Ala Ile Ser Gln Ile Gln Glu Ser Leu Thr Thr Thr
        50                  55                  60

Ser Thr Ala Leu Gly Lys Leu Gln Asp Val Val Asn Gln Asn Ala Gln
65                  70                  75                  80

Ala Leu Asn Thr Leu Val Lys Gln Leu Ser
                85                  90
```

<210> SEQ ID NO 4
<211> LENGTH: 101
<212> TYPE: PRT
<213> ORGANISM: SARS coronavirus

<400> SEQUENCE: 4

```
Ser Asn Phe Gly Ala Ile Ser Ser Val Leu Asn Asp Ile Leu Ser Arg
1               5                   10                  15
```

-continued

```
Leu Asp Lys Val Glu Ala Glu Val Gln Ile Asp Arg Leu Ile Thr Gly
        20                  25                  30

Arg Leu Gln Ser Leu Gln Thr Tyr Val Thr Gln Gln Leu Ile Arg Ala
        35                  40                  45

Ala Glu Ile Arg Ala Ser Ala Asn Leu Ala Ala Thr Lys Met Ser Glu
    50                  55                  60

Cys Val Leu Gly Gln Ser Lys Arg Val Asp Phe Cys Gly Lys Gly Tyr
65                  70                  75                  80

His Leu Met Ser Phe Pro Gln Ala Ala Pro His Gly Val Val Phe Leu
                85                  90                  95

His Val Thr Tyr Val
            100
```

<210> SEQ ID NO 5
<211> LENGTH: 219
<212> TYPE: DNA
<213> ORGANISM: Artificial
<220> FEATURE:
<223> OTHER INFORMATION: Modified sequence encoding partial SARS E2
    spike protein.

<400> SEQUENCE: 5

```
aacaccatcg ctatcccgac caacttctcc atctccatca ccaccgaagt tatgccggtt    60
tccatggcta aaacctccgt tgactgcaac atgtacatct gcggtgactc caccgaatgc   120
gctaacctgc tgctgcagta cggttccttc tgcacccagc tgaaccgtgc tctgtccggt   180
atcgctgctg aacaggaccg taacacccgt gaataatag                          219
```

<210> SEQ ID NO 6
<211> LENGTH: 297
<212> TYPE: DNA
<213> ORGANISM: Artificial
<220> FEATURE:
<223> OTHER INFORMATION: Modified sequence encoding partial SARS E2
    spike protein.

<400> SEQUENCE: 6

```
gttttcgctc aggttaaaca gatgtacaaa accccgaccc tgaaatactt cggtggtttc    60
aacttctccc agatcctgcc ggacccgctg aaaccgacca acgttccctt catcgaagac   120
ctgctgttca acaaagttac cctggctgac gctggtttca tgaaacagta cggtgaatgc   180
ctgggtgaca tcaacgctcg tgacctgatc tgcgctcaga aattcaacgg tctgaccgtt   240
ctgccgccgc tgctgaccga cgacatgatc gctgcttaca ccgctgctct gtaatag      297
```

<210> SEQ ID NO 7
<211> LENGTH: 276
<212> TYPE: DNA
<213> ORGANISM: Artificial
<220> FEATURE:
<223> OTHER INFORMATION: Modified sequence encoding partial SARS E2
    spike protein.

<400> SEQUENCE: 7

```
gtttccggta ccgctaccgc tggttggacc ttcggtgctg gtgctgctct gcagatcccg    60
ttcgctatgc agatggctta ccgtttcaac ggtatcggtg ttacccagaa cgttctgtac   120
gaaaaccaga acagatcgc taaccagttc aacaaagcta tctcccagat ccaggaatcc   180
ctgaccacca cctccaccgc tctgggtaaa ctgcaggacg ttgttaacca gaacgctcag   240
gctctgaaca ccctggttaa acagctgtcc taatag                             276
```

<210> SEQ ID NO 8
<211> LENGTH: 309
<212> TYPE: DNA
<213> ORGANISM: Artificial
<220> FEATURE:
<223> OTHER INFORMATION: Modified sequence encoding SARS E2 spike
      protein.

<400> SEQUENCE: 8

```
tccaacttcg gtgctatctc ctccgttctg aacgacatcc tgtcccgtct ggacaaagtt      60
gaagctgaag ttcagatcga ccgtctgatc accggtcgtc tgcagtccct gcagacctac     120
gttacccagc agctgatccg tgctgctgaa atccgtgctt ccgctaacct ggctgctacc     180
aaaatgtccg aatgcgttct gggtcagtcc aaacgtgttg acttctgcgg taaaggttac     240
cacctgatgt ccttcccgca ggctgctccg cacggtgttg ttttcctgca cgttacctac     300
gtttaatag                                                              309
```

<210> SEQ ID NO 9
<211> LENGTH: 1255
<212> TYPE: PRT
<213> ORGANISM: SARS coronavirus

<400> SEQUENCE: 9

```
Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255
```

-continued

Leu Lys Pro Thr Thr Phe Met Leu Lys Tyr Asp Glu Asn Gly Thr Ile
        260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
        290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
        340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
        370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
                420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
        450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
                500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
        530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ala Phe Gly Gly Val Ser Val Ile Thr Pro Gly Thr Asn Ala Ser Ser
                580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
        610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
        660                 665                 670

```
Ser Ile Val Ala Tyr Thr Met Ser Leu Gly Ala Asp Ser Ile Ala
        675                 680                 685

Tyr Ser Asn Asn Thr Ile Ala Ile Pro Thr Asn Phe Ser Ile Ser Ile
        690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
        770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
        930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys Met Ser Glu Cys Val  Leu Gly Gln Ser Lys  Arg Val Asp
        1010                1015                1020

Phe Cys Gly Lys Gly Tyr His  Leu Met Ser Phe Pro  Gln Ala Ala
        1025                1030                1035

Pro His Gly Val Val Phe Leu  His Val Thr Tyr Val  Pro Ser Gln
        1040                1045                1050

Glu Arg Asn Phe Thr Thr Ala  Pro Ala Ile Cys His  Glu Gly Lys
        1055                1060                1065

Ala Tyr Phe Pro Arg Glu Gly  Val Phe Val Phe Asn  Gly Thr Ser
        1070                1075                1080

Trp Phe Ile Thr Gln Arg Asn  Phe Phe Ser Pro Gln  Ile Ile Thr
```

-continued

```
              1085                1090                1095
Thr  Asp  Asn  Thr  Phe  Val  Ser  Gly  Asn  Cys  Asp  Val  Val  Ile  Gly
              1100                1105                1110

Ile  Ile  Asn  Asn  Thr  Val  Tyr  Asp  Pro  Leu  Gln  Pro  Glu  Leu  Asp
              1115                1120                1125

Ser  Phe  Lys  Glu  Glu  Leu  Asp  Lys  Tyr  Phe  Lys  Asn  His  Thr  Ser
              1130                1135                1140

Pro  Asp  Val  Asp  Leu  Gly  Asp  Ile  Ser  Gly  Ile  Asn  Ala  Ser  Val
              1145                1150                1155

Val  Asn  Ile  Gln  Lys  Glu  Ile  Asp  Arg  Leu  Asn  Glu  Val  Ala  Lys
              1160                1165                1170

Asn  Leu  Asn  Glu  Ser  Leu  Ile  Asp  Leu  Gln  Glu  Leu  Gly  Lys  Tyr
              1175                1180                1185

Glu  Gln  Tyr  Ile  Lys  Trp  Pro  Trp  Tyr  Val  Trp  Leu  Gly  Phe  Ile
              1190                1195                1200

Ala  Gly  Leu  Ile  Ala  Ile  Val  Met  Val  Thr  Ile  Leu  Leu  Cys  Cys
              1205                1210                1215

Met  Thr  Ser  Cys  Cys  Ser  Cys  Leu  Lys  Gly  Ala  Cys  Ser  Cys  Gly
              1220                1225                1230

Ser  Cys  Cys  Lys  Phe  Asp  Glu  Asp  Asp  Ser  Glu  Pro  Val  Leu  Lys
              1235                1240                1245

Gly  Val  Lys  Leu  His  Tyr  Thr
              1250                1255
```